US00PP21934P3

(12) United States Plant Patent
Crocker

(10) Patent No.: US PP21,934 P3
(45) Date of Patent: May 31, 2011

(54) ALMOND TREE, 'SUPAREIL'

(50) Latin Name: *Prunus dulcis*
Varietal Denomination: Supareil

(76) Inventor: Bill Crocker, Chico, CA (US)

( * ) Notice: Subject to any disclaimer, the term of this patent is extended or adjusted under 35 U.S.C. 154(b) by 0 days.

(21) Appl. No.: 12/590,386

(22) Filed: Nov. 5, 2009

(65) Prior Publication Data

US 2011/0107478 P1 May 5, 2011

(51) Int. Cl.
*A01H 5/00* (2006.01)

(52) U.S. Cl. ..... Plt./155

(58) Field of Classification Search ..... Plt./155
See application file for complete search history.

*Primary Examiner* — Annette H Para

(74) *Attorney, Agent, or Firm* — Paine Hamblen, LLP

(57) ABSTRACT

A new and distinct variety of almond tree is described and which is somewhat similar to the 'Nonpareil' almond tree (non-patented), but which is distinguishable therefrom by producing a larger sized kernel of high quality and having a sweet flavor when compared to the with 'Nonpareil' almond tree (non-patented).

1 Drawing Sheet

BACKGROUND OF THE NEW VARIETY

The present invention relates to a new and distinct variety of almond tree, *Prunus dulcis,* which will hereinafter be denominated varietally as 'Supareil' and more specifically to an almond tree which produces nuts for commercial harvesting, hulling, shelling and shipment during the first week of September, that is during September 3-7$^{th}$ under the ecological conditions prevailing in the vicinity of Livingston, Calif. which is in the central part of the San Joaquin Valley of California. The present variety is also noteworthy for producing a soft-shelled almond with flavor characteristics which are considered to be excellent.

In the evaluation of almond tree varieties there is a number of criteria which are utilized to determine whether a new almond tree very will have commercial success. As a general matter, new trees and their crops are usually evaluated on the basis of their ripening date, flavor, texture, storage and shipping quality. With almonds, as with other produce, the date of ripening, the quality of the meat of the kernel, freedom from unusual numbers of doubles, as well as a soft shell makes a new variety commercially attractive, with a substantial likelihood of commercial success. It has long been known that almond tree varieties that produce a soft shell as opposed to hard shell nuts make the kernel removal much easier. Therefore, the ease of shelling, and the high quality of the kernel, plus a low percentage of doubles gives the present almond an excellent appeal to the distributor and consumer, alike. In relative comparison to other known varieties of almond trees, the present variety is clearly distinguishable. In this regard, and in relative comparison to the 'Nonpareil' almond tree (unpatented), and the 'Carmel' almond tree (U.S. Pat. No. 2,641), the present variety is clearly distinguishable by its date of harvesting (about 10 days later) and its excellent flavor. Further, in relative comparison to other nut varieties such as U.S. Plant Pat. No. 19,369, the present variety is distinguishable therefrom by its date of harvesting which is some two weeks later than the date of harvesting of aforementioned patented variety. Also, in relative comparison to the 'Nonpareil' variety, it has been observed that the present variety produces nut meat having a sweeter quality and a kernel which is slightly lighter in color, and larger in size.

ORIGIN AND ASEXUAL REPRODUCTION OF THE NEW VARIETY

The present variety of almond tree was discovered by the inventor in the late 1990's as a chance seedling of unknown parentage then growing within a cultivated region of his 'Nonpareil' (unpatented) almond orchard which is located near Chico, Calif. in the Northern Sacramento Valley. After several years of observation, the inventor determined that additional almond trees should be asexually propagated of this new variety to determine whether the observed characteristics of the newly discovered chance seedling would be true across multiple generations. In this regard, the inventor contracted to have a local nursery in Oakdale, Calif. asexually reproduce 500 trees onto Nemaguard (unpatented rootstock) for further planting and observation. These asexually reproduced trees were then planted in 2002 and have been continually observed by the inventor since that time. Further, during this analysis period, the nut characteristics as well as the kernel characteristics of the new variety were studied. Based upon all the collective observations made of this first group of asexually reproduced trees, it has been determined that these asexually reproduced trees appear to be identical to the original chance seedling which was found in the late 1990's in all respects. These first asexually reproduced trees were planted in an almond orchard then located in Livingston, Calif. This first group of asexually reproduced trees are now in their seventh leave. Further, it has been confirmed that the vigor of these trees is quite similar to the 'Nonpareil' almond trees growing in the same geographical vicinity.

SUMMARY OF THE VARIETY

The present variety of almond tree 'Supareil' is characterized as to novelty by producing a soft shell, well sealed almond which somewhat resembles the nut provided by the 'Nonpareil' almond tree (unpatented), but which is distinguishable therefrom, and characterized principally as to novelty by being mature for commercial harvesting, hulling, shelling and shipment during the first week of September, that is, September $3^{rd}$-$7^{th}$ under the ecological conditions prevailing near Livingston, Calif. The new variety of almond tree while somewhat similar in some of its characteristics to that of the 'Nonpareil' almond tree (unpatented), is distinguishable therefrom by producing a nut having a sweeter quality meat, a kernel which is slightly lighter in color, and larger in size, and which further is harvested about 10 days later than the unpatented 'Nonpareil' almond tree when grown at the same geographical location and under similar cultural conditions.

BRIEF DESCRIPTION OF THE DRAWINGS

The accompanying drawing which is provided is a color photograph of the new variety of almond tree. The color photograph depicts one branch of the present variety displaying its growth characteristics with almonds sufficiently matured for harvesting and shipment. Further, a twig bearing typical leaves showing the dorsal and ventral coloration thereof is also depicted. Additionally, several leaves showing the dorsal and ventral coloration are also displayed. In addition to the foregoing, six shelled almonds and their associated kernels are shown and which display the side view, overall shape, and suture characteristics thereof. The colors in this photograph are nearly as true as is reasonably possible in a color representation of this type. Due to chemical development, processing and printing, the leaves and nut crop depicted in these photographs mayor may not be accurate when compared to the actual specimen. For this reason, future color references should be made to the color plates as provided by The Royal Horticultural Society Colour Chart, 4th Edition.

DETAILED DESCRIPTION

Referring more specifically to the horticultural details of this new and distinct variety of almond tree, the following has been observed under the ecological conditions prevailing near Livingston, Calif. All major color code designations are by reference to The Royal Horticultural Society Colour Chart, $4^{th}$, 2001 Edition. Additionally, common color names are also used occasionally.

NOT A COMMERCIAL WARRANTY

The following detailed description has been prepared to solely comply with the provisions of 35 U.S.C. § 112, and does not constitute a commercial warranty, (either expressed or implied), that the present variety will in the future display the botanical, or other observed characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

TREE

*Origin.*—The present variety was discovered as a chance seedling of unknown parentage and which was found within the cultivated area of a 'Nonpareil' (unpatented) almond orchard. The trees which were studied for this application were in their seventh leaf. All the present trees were asexually reproduced at an orchard near Oakdale, Calif.

*Vigor.*—Considered vigorous.

*Chilling requirement.*—Normal under typical San Joaquin Valley climatic conditions.

*Tree figure.*—Considered spreading and upright in its growth pattern. Typical height of the tree is about 16-18 feet for trees in their seventh leaf.

*Tree canopy.*—Width — About 15-16 feet.

*Crotch angle.*—Approximately 81°. This is a non-distinguishing characteristic of the tree, however.

*Productivity.*—Considered very productive under typical San Joaquin Valley climatic conditions.

*Regularity of bearing.*—Considered regular for the species.

TRUNK

*Size.*—Large.

*Trunk circumference.*—About 31 inches when measured at a distance of 12 inches above the graft.

*Trunk texture.*—Considered rough.

*Trunk color.*—Grey, RHS Grey-Brown 199(A).

*Trunk lenticels.*—Considered profuse.

BRANCHES

*Generally.*—Size — On trees that are in their $7^{th}$ leaf, the branches are considered large, that is, they are typically 15.5 inches in circumference.

*Surface texture.*—Mature branches — The surface texture is considered slightly rough.

*Surface texture.*—Immature branches — Considered smooth.

*Bark color.*—1 year or older wood — Grey-Brown RHS 199 (C).

*Bark color.*—Immature branches — Yellow-Green RHS 147 (D).

*Bark lenticels.*—On the branches which were examined at least 20 lenticels will be found over a 4 inch region of the primary scaffold branches. The branches of the present variety have an internode length of about 2 cm. when measured at mid-branch.

LEAVES

*Size.*—Generally — Considered large for the species. The leaf arrangement for the present variety is alternate.

*Length.*—About 97 mm. to about 107 mm.

*Width.*—About 23 mm. to about 27 mm.

*Leaf shape.*—Lanceolate.

*Leaf thickness.*—Considered normal for the species.

*Leaf color.*—Upper surface — Green, RHS 136 (B).

*Leaf color.*—Downwardly disposed surface — Light Green, RHS 138 (B).

*Leaf marginal form.*—Crenulate.

*Leaf vein.*—Color — Yellow-Green, RHS 145 (A). The leaf venation pattern is pinnate.

*Petiole.*—Length — About 15 mm. to about 20 mm.

*Petiole.*—Color — Yellow-Green, RHS 144 (A).

*Petiole.*—Sinus shape — Semi-rounded.

*Stipules.*—Numbers — 1-2 may be found.

*Stipules.*—Size — Small. About 2 mm.

*Stipules.*—Color — Grey-Purple, RHS 183 (B).

*Stipules.*—Arrangement — Considered opposite.

FLOWER

*Date of bloom.*—Observed between February 22$^{nd}$ and February 28$^{th}$ during the 2009 growing season. Approximately 50% of the bloom was achieved by February 22, and full bloom was observed on February 28$^{th}$.

*Bloom amount.*—Considered abundant.

*Flowers observed per node.*—1-3 flowers may be found.

*Bloom color.*—Considered Light Pink, RHS 69 (C).

*Bloom diameter.*—About 38 mm. to about 50 mm.

*Flower petals.*—Marginal form — Slightly undulate. Some apex notching may be seen.

*Flower petals.*—Length — About 17-22 mm.

*Flower petals.*—Width — About 14-16 mm.

*Sepals.*—Numbers — 5 are typically seen.

*Sepals.*—Size — About 6-8 mm. in length; and 5 mm. in width.

*Sepals.*—Color — The basal end is Green, RHS 114 (B).

*Sepals.*—Color — The apical end is RHS 183 (C).

*Sepals.*—Shape — Conic.

*Pistil.*—Length — About 14-16 mm.

*Anthers.*—Length — About 1-2 mm.

*Anthers.*—Color — Grey-Yellow, RHS 162 (A).

*Pollen.*—Amount — Abundant.

*Pollen.*—Color — Yellow-Orange, RHS 25 (B).

*Stamens.*—Numbers — About 24-30.

*Stamens.*—Length — About 5-12 mm.

*Stamens.*—Color — Grey-White RHS 155 (C).

*Pedicel.*—Length — About 1½ to about 4 mm.

*Pedicel.*—Color — Yellow-Green, RHS 144 (D).

*Flower buds.*—Size — About 4-6 mm. in length. Flower bud width — about 3 to about 3.5 mm.

*Flower buds.*—Shape — Conic. Flower bud length — about 4 mm. to 6 mm. Flower bud diameter — about 3 mm. to about 3.5 mm.

*Flower buds.*—Color — Grey-Orange RHS 75 (A) when observed at the basal end; and approximately Grey-Orange RHS 165 (B) when seen at the central end of the bud scale.

CROP

*Regularity of bearing.*—Considered regular.

*Productivity.*—Considered very good for the species.

*Harvesting date.*—During the first week of September, which is approximately September 3-September 7 under the ecological conditions prevailing near Livingston, Calif. The harvesting date is 10 days after the 'Nonpareil' almond variety at the same geographical location.

*Nut distribution.*—Considered well distributed throughout the tree.

*Tenacity.*—Considered good for the species.

NUT

*Nut size.*—Length — about 39.3 mm; Nut Width — about 23.5 mm.

*Nut.*—Thickness — about 16 mm.

*Nut shape.*—Ovate.

*Surface texture.*—Outer shell — Flaked, and covered with randomly spaced round pits.

*Surface texture.*—Inner shell — Brittle, but considered smooth.

*Nut color.*—Outer Shell Surface — RHS Grey-Orange Group 164 (C); Inner Shell Surface — RHS Grey-Orange Group 165 (C).

*Stem attachment point.*—Size — Considered small, and minimal, and not prominent relative to the nut.

*Nut apex.*—Shape — Sharply pointed.

*Nut wing.*—Generally considered prominent; Inner surface — considered smooth.

*Percentage of kernel to overall nut.*—Approximately 50-66%.

*Shell thickness.*—About 2-5 mm.

KERNEL

*Size.*—Length — About 26 mm. to about 30 mm.

*Size.*—Width — About 15 mm.

*Kernel shape.*—Ovate.

*Kernel thickness.*—About 8 mm. to about 10 mm.

*Kernel base.*—Shape — Somewhat flat.

*Kernel apex.*—Shape — Sharply acute.

*Kernel surface texture.*—Slightly ribbed.

*Kernel pubescence.*—Not evident.

*Kernel color.*—Grey-Orange, RHS N170 (B).

*Number of doubles produced.*—Of 79 specimens inspected, only 2 included doubles. This represented approximately a 2.5% rate for doubling.

*Kernel flavor.*—Generally — Considered sweet, and very good, and superior to that of the nut produced by the 'Nonpareil' almond tree (unpatented) which is growing in the same vicinity.

*Storage quality.*—Considered very good for the species in relative comparison to other varieties growing in the same geographical area.

*Resistance to disease.*—This variety appears to be resistant to anthracruss.

*Pollination requirements.*—This variety appears to need a pollinator. The nut variety 'Aldrich' (non-patented); and 'Nonpareil' (non-patented) appear to be good pollinators.

*Average kernel weight.*—About 1.47 grams/kernel. This characteristic does not distinguish the present variety from other known varieties because this characteristic is dependent, in part, on the cultural conditions under which the tree was grown.

*Kernel size.*—Generally speaking, and in relative comparison to the 'Nonpareil' almond tree (non-patented), the kernel produced by the present variety of almond tree is slightly larger in size than that produced by the 'Nonpareil' variety under similar ecological conditions. Further, the new variety of almond tree produces a kernel which is different in color and further has a flavor that is sweeter and distinctive from the crop produced by the 'Nonpareil' almond tree (non-patented), and which is growing in the same geographical area. Still further, in view of the low percentage of doubles that the present variety produces, this new variety of almond tree would appear to be quite distinctive and novel in relative comparison to the 'Nonpareil' almond tree (non-patented) which are growing in the same geographical area and which are mature for harvesting approximately 10 days earlier then this new variety.

Although the new variety of almond tree possess the described characteristics noted above, as a result of the growing conditions prevailing in the central part of the San Joaquin Valley of Central California, it is to be understood that characteristics of the usual magnitude incident to changes in growing condition, fertilization, pruning and pest control are to be expected.

Having thus described and illustrated my new variety of almond tree, what I claim is new, and desire to secure by plant Letters Patent is:

1. A new and distinct variety of almond tree as substantially shown and described, and which is somewhat similar to the 'Nonpareil' almond tree (non-patented), but which is distinguishable therefrom by producing a slightly larger, and slightly lighter colored kernel of high quality, with a soft shell, and which is further mature for harvesting and shipment about September 3-September 7 under the ecological conditions prevailing near Livingston, Calif.

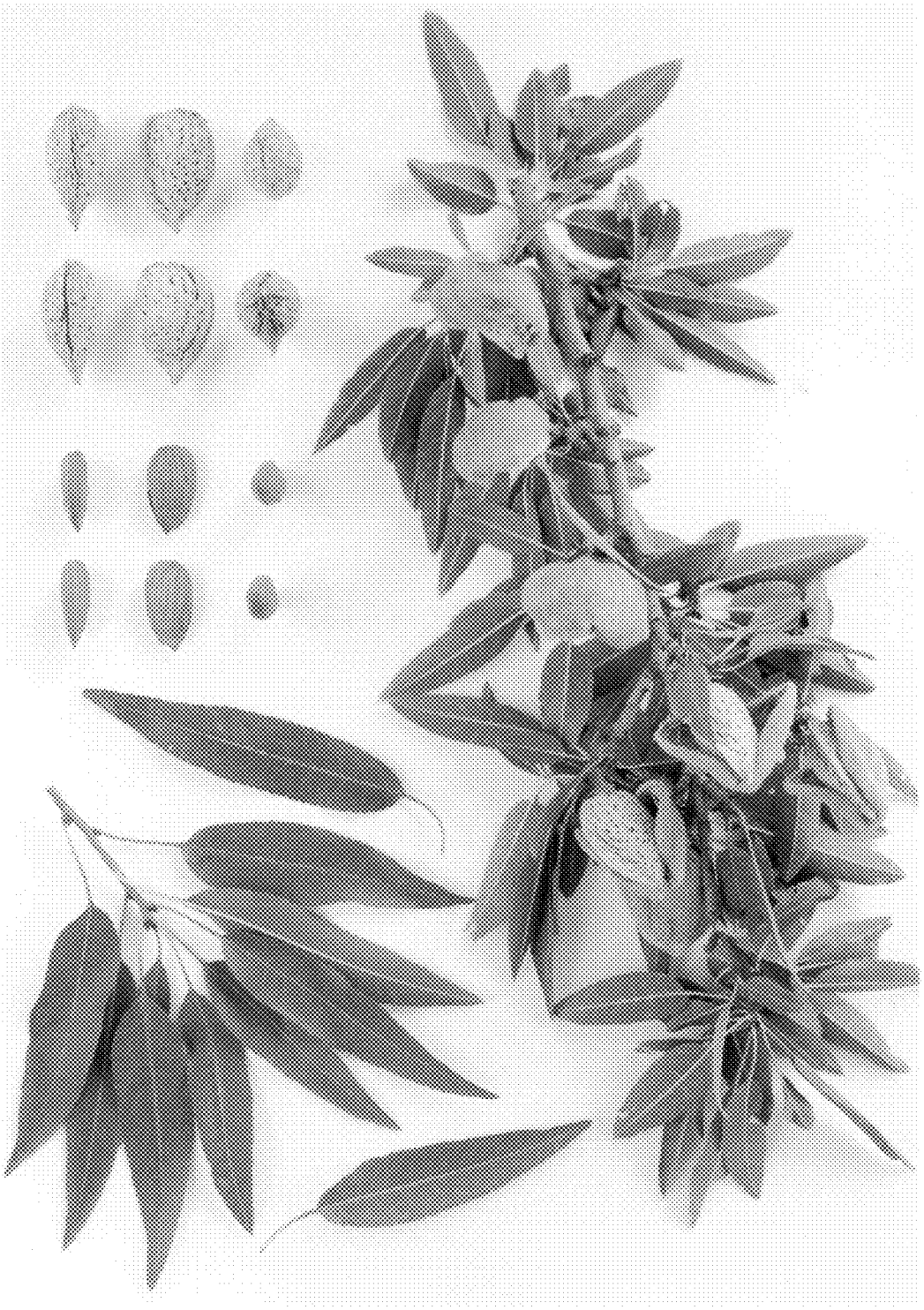

* * * * *